(12) United States Patent
Protogirou

(10) Patent No.: US 6,224,600 B1
(45) Date of Patent: May 1, 2001

(54) INTRAMEDULLARY, FLEXIBLE FRACTURE FIXATION DEVICE, USING BI-AXIAL PRESTRESSING

(76) Inventor: G. Constantine Protogirou, 9, Pigassou Street, I54 52 P. Psichiko, Athens (GR)

(*) Notice: Subject to any disclaimer, the term of this patent is extended or adjusted under 35 U.S.C. 154(b) by 0 days.

(21) Appl. No.: 09/214,600
(22) PCT Filed: Jul. 9, 1997
(86) PCT No.: PCT/GR97/00026
  § 371 Date: Mar. 5, 1999
  § 102(e) Date: Mar. 5, 1999
(87) PCT Pub. No.: WO98/01077
  PCT Pub. Date: Jan. 15, 1998

(30) Foreign Application Priority Data

Jul. 10, 1996 (GB) .............................................. 960100234

(51) Int. Cl.[7] .................................................. A61B 17/18
(52) U.S. Cl. ................................................. 606/63; 606/68
(58) Field of Search ................................ 606/62, 63, 64, 606/65, 66, 67, 68

(56) References Cited

U.S. PATENT DOCUMENTS

| | | | |
|---|---|---|---|
| 4,236,512 | * 12/1980 | Aginsky | 606/63 |
| 4,632,101 | * 12/1986 | Freeland | 606/63 |
| 5,057,103 | * 10/1991 | Davis | 606/63 |
| 5,603,715 | * 2/1997 | Kessler | 606/63 |

FOREIGN PATENT DOCUMENTS

| | | | |
|---|---|---|---|
| 923085 | * 2/1955 | (DE) | 606/63 |
| 2657303 | * 6/1977 | (DE) | 606/63 |
| 689800 | * 1/1996 | (EP) | 606/63 |
| 2268068 | * 1/1994 | (GB) | 606/63 |

* cited by examiner

Primary Examiner—Pedro Philogene
(74) Attorney, Agent, or Firm—Blank Rome Comisky & McCauley LLP

(57) ABSTRACT

The invention refers to a prosthetic device for the application of simultaneous axial and transversal prestressing to obtain stable and elastic osteosynthesis of fractures. The device focuses on the concept of internal fixation with consideration for the natural frequency of the bone. The device for fracture fixation comprises a "tendon" (i.e, a tensionable wire) least one deformable element at the focus of the fracture, with the tendon and the deformable element being disposed almost parallel, whereby the device further comprises compression means to apply a compression force to the deformable element(s), so that the deformable element (s) deform(s) laterally. The device described can be used for fractures of long bones as well as for proximal femoral fractures. When used for long bone fractures, the device is an intramedullar flexible bar, with which we apply adjustable and measurable axial prestressing in order to compress the bone fragments and preload the bone. When used for proximal femoral fractures, the device is the same intramedullar flexible bar, with which we apply adjustable and measuring lateral prestressing while anchoring it on the femoral shaft exterior. By doing so we compress the bone fragments in order to neutralize the tension forces on the fracture and to avoid interfragmentary motions. The terms "axial prestressing" and "lateral prestressing" refer to axis long bone. The device allows us to achieve predetermined and measurable intramedullar transversal prestressing, which is a prerequisite for the application of axial prestressing.

12 Claims, 4 Drawing Sheets

FIG. 5
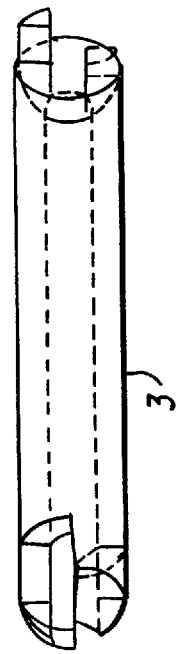
FIG. 7
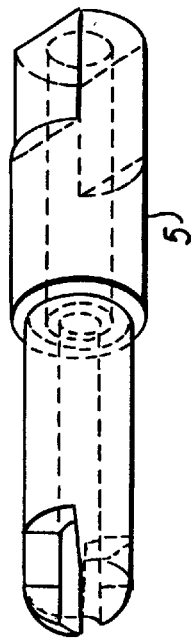
FIG. 6
FIG. 12
FIG. 11
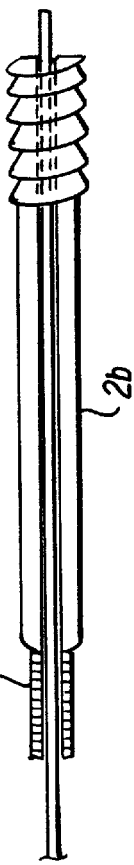
FIG. 10

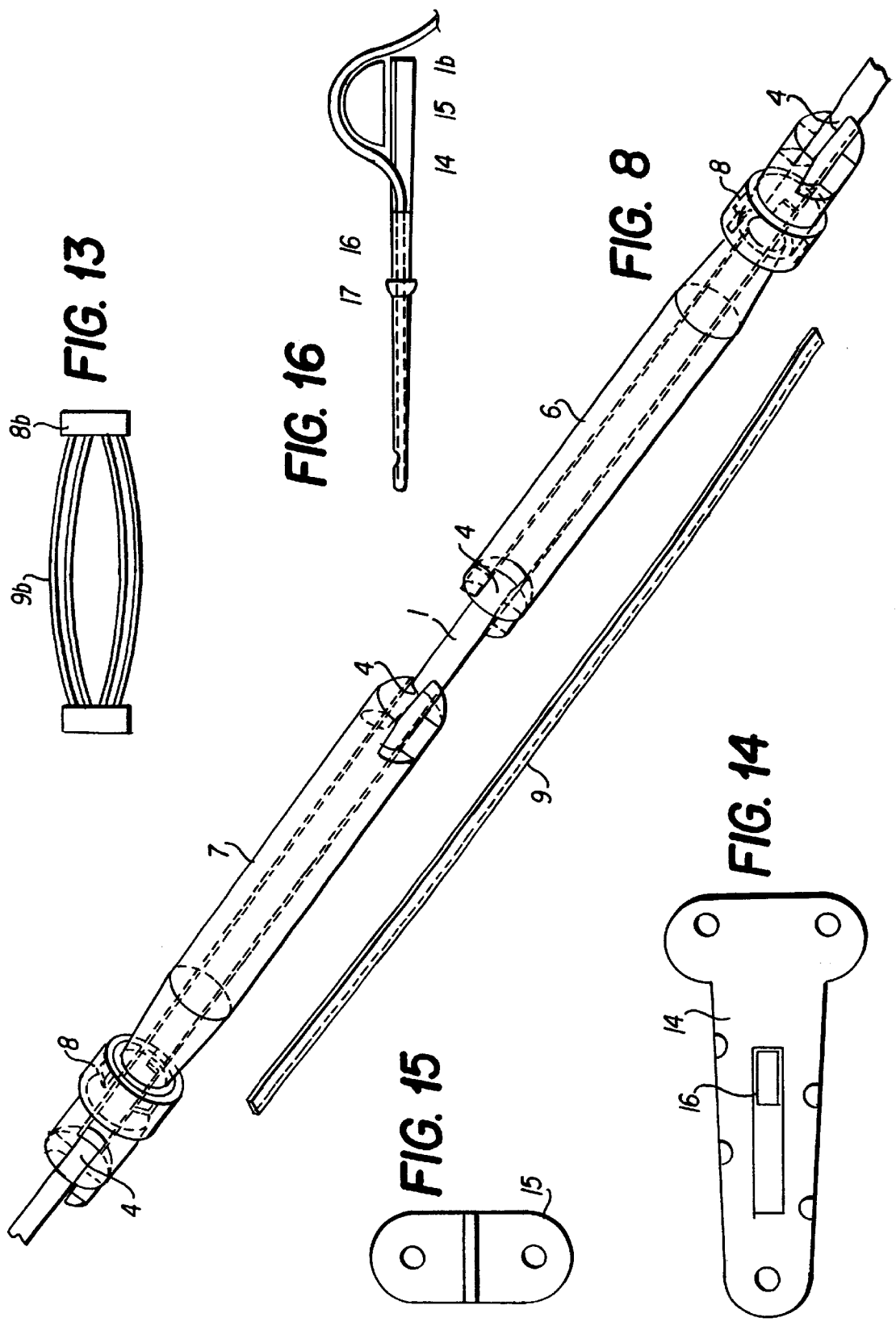

INTRAMEDULLARY, FLEXIBLE FRACTURE FIXATION DEVICE, USING BI-AXIAL PRESTRESSING

BACKGROUND OF THE INVENTION

The invention refers to a device for fracture fixation. Devices for fracture fixation are known from EP 0 698 800, which discloses affixing an elongated rod on the bone. Further, documents GB 2 268 068 and DE 923 085 disclose devices for fracture fixation comprising at least a deformable element and compression means to apply a compression force to the deformable element, so the deformable element deforms laterally.

Each of the well established fixation methods (rigid compression planting, reamed intramedullary nailing, with or without interlocking of the fracture fragments, external fixation and dynamic hip screw) has advantages and disadvantages as well as special biomechanical characteristics. Vast clinical experience combined with the data produced from theoretical and experimental studies have described many of the problems related to the biomechanics of these fracture fixation devices.

Today's understanding of bone biology has led us to a new approach to bone fixation. This approach considers the importance of the preservation of the soft tissue and of careful protection of the viability of bone. This invention aims to add to the theory and practice of bone fixation the concept that the fracture fixation device introduces into the broken bone equilibrium tensions to restore the intraosseous forces and make the bone capable of receiving the load stresses and muscle-spasm stresses right at the beginning of the healing period, as opposed to the prior concept that it is the device that receives these stresses.

A first attempt towards these goals is disclosed by Protogirou in PCT International Publication Number WO 91/19461 (title: Device for Osteosynthesis with Axially Guided Prestressing Elements). This device was also trying to solve some of the problems related to the biomechanics of bone fixation using axial prestressing to achieve stable and elastic osteosynthesis thus restoring the intraosseous forces. The resetting of the fragments remains stable by the medullary guide and the axial prestressing is applied through the tendons.

SUMMARY OF THE INVENTION

According to the invention the device for fracture fixation comprises, a tendon and at least a deformable element at the focus of the fracture, whereby the deformable elements may be 2, 3, 4, 5, or more, with the tendon and the deformable element being disposed almost along the same direction, whereby the device further comprises compression means to apply a compression force to the deformable elements, so that the deformable elements deforms laterally. The device described can be used for fractures of long bones as well as for proximal femoral fractures. When used for long bone fractures, the device is an intramedullar flexible bar, by which is applied adjustable and readable axial prestressing in order to compress the bone fragments and preload the bone, and not a supportive intramedullar nail as the devices used sofar for fracture fixation. When used for proximal femoral fractures, the device is the same intramedullar flexible bar, by which is applied adjustable and readable lateral prestressing when anchoring it on the external femoral shaft. By doing so the bone fragments are compressed in order to neutralize the tension forces on the fracture and to avoid the interfragments motions. The terms "axial prestressing" and "lateral prestressing" refer to the axis of the long bone.

With the prosthetic device of the invention it is possible to apply simultaneously axial and transversal pre-stressing to pre-load the bone and obtain stable and elastic osteosynthesis of fractures. The device focuses on the concept of biological internal fixation with minimal damage and with consideration for the natural frequency of the bone.

The device according to the invention presents a different approach to the problem of fracture fixation in that it allows achievement of predetermined and readable intramedullar transversal prestressing, which is a prerequisite for the application either of axial prestressing or of lateral prestressing. The transversal prestressing holds in place the repositioned bone fragments and contributes to the neutralization of the bending moments and the shearing forces between the fracture angle and the mechanical axis of the bone caused by the axial prestressing in the case of long bone fractures. In the case of proximal femoral fractures the transversal prestressing diminishes the interfragmentary motions. The term "transversal prestressing" refers to the "axial prestressing" and the "lateral prestressing" and is vertical to them.

Moreover, because the transversal prestressing can diminish the bending moments and the shearing forces caused by muscular spasm, the same device can be used as bone distractor for unstable long bone fractures.

The ability to compress the bone ends uniformly, In the case of long bone fractures, can be achieved through intramnedullary axial prestressing. But the fractured bone cannot receive compression forces if it is not repositioned in a stable way, because of bending and shearing forces occurring as a result of compression. The resetting of the fragments remains stable and allows for the application of axial prestressing because of the prior application of intramedullary transversal prestressing. In order to achieve this bi-axial prestressing a tendon is inserted intremedullarly and anchored in the one end of the bone. The tendon is passing through cylindrical bodies, which fit into one another and form a flexible bar. At least one pair of cylindrical bodies bear attachment means for deformable elements. By applying compression to the cylinders by the compression nut the cylinders we brought together and compress the deformable elements, which deform laterally and exercise pressure on the inner wall of the bone (transversal prestressing). As the tendon is already anchored in the one end of the bone, tension is exercised on the tendon by a screw bolt with support on an anchor means, which is anchored into the other end of the bone (axial prestressing). In spite of the application of tension, the flexible bar does not become a straight bar, but on the contrary it follows all the curvatures of the bone.

The neutralization of tension forces on the fractured proximal femoral bone can be achieved through lateral prestressing (tension band). The application of lateral prerstressing becomes more efficient if the interfragmentary motions are diminished. This is achieved by the prior application of transversal prestressing. In order to achieve this double prestressing an anchor screw is anchored in the head of the femur. The other end of this anchor screw is formed as a cylinder with attachment means at both its ends for the deformable elements. By applying compression to a compression means at the end of the cylinder other than the end bearing the screw, the deformable elements are compressed, which deform laterally and exercise pressure on the inner wall of the bone (transversal prestressing). The one end of the tendon is anchored at the end of the cylinder other than the end bearing the screw. The tendon is anchored by a ball means in order to form an articulation at this point and thus diminish the motion between implant and bone.

The tendon bends on the lateral femoral shaft with support on a fulcrum attached on a plate, which plate is screwed in the lateral femoral shaft. The other end of the tendon passes through a cylinder fixed to the plate. Tension is exercised on this end of the tendon with support on the cylinder fixed to the plate and the tendon is then anchored on the plate (lateral prestressing). In some cases of unstable fractures a second tension band (wire) is added to the above described device ends of the wire are introduced in the form of a slip knot into the bone from the opening made for the anchor means 2b, towards the base of the femoral neck. The slip knot is then anchored on the anchor screw, tightened over the greater trochanter, and both its ends then anchored on the plate.

The following advantages can be observed compared with the previous fixation methods (rigid compression plating, reamed intramedullary nailing with or without interlocking of the fragments, external fixation and dynamic hip screw):

The resetting of the fragments is supported by the transversal prestressing.

One does not have to operate at the fracture area because the device is inserted intramedullary by the same technique as any intramedullary nail in the cases of long bone fractures, and it is inserted from the lateral femoral shaft by the same technique as the present devices in the cases of proximal femur fractures.

The device is introduced without any reaming, and fills up the intramedullar area, thus allowing for early bearing.

The device is inserted easily and it does not affect the shape of the bone because it is flexible and self guided and follows the curves of the bone.

Friction between device and bone is minimal because of small and firm contact between them.

The infection possibility and other complications are minimised.

The time of medical attendance and recovery is minimised.

The removal of the device is very easy.

Moreover, because the transversal prestressing can neutralism the bending moments and the shearing forces caused by muscular spasm, the same device can be used as bone distractor for unstable fractures.

The possible mistakes are very few because the method is easy to learn and apply.

The use of x-rays is not necessary in many cases, and when indispensable, the time of use is minimized.

The device does not affect the E-modulus and the blood circulation of the bone.

it is possible to assemble Individual device components of different lengths, so as to achieve adjustment according to the geometry of the specific bone (Universal and Modular).

BRIEF DESCRIPTION OF THE DRAWINGS

The present invention will be better understood with the following detailed description of an embodiment for each type of fracture, long bone and proximal femur fracture, in connection with the accompanying drawings:

FIG. 5 is a representation of the tendon 1 with anchor means 2 at its one end and screw means 2a at its other end.

FIG. 6 is a representation of torque means 5.

FIG. 7 is a representation of a cylindrical element 3.

FIG. 8 is a representation of the two cylindrical elements 6 and 7, and of the deformable element 9.

FIG. 10 is a representation of the anchor means 2b.

FIG. 11 is a representation of a bolt 18.

FIG. 12 is a representation of the end of the tendon 1b, which end is formed as a ball.

FIG. 13 is a representation of the deformable elements 9b attached to the attachment means 8b.

FIG. 14 is a representation of the plate 14 with the cylinder 16.

FIG. 15 is a representation of the protrusion 15S, which is attached to the head of the plate 14.

FIG. 16 is a section of the plate 14.

DETAILED DESCRIPTION OF THE PREFERRED EMBODIMENTS

Figure 1:
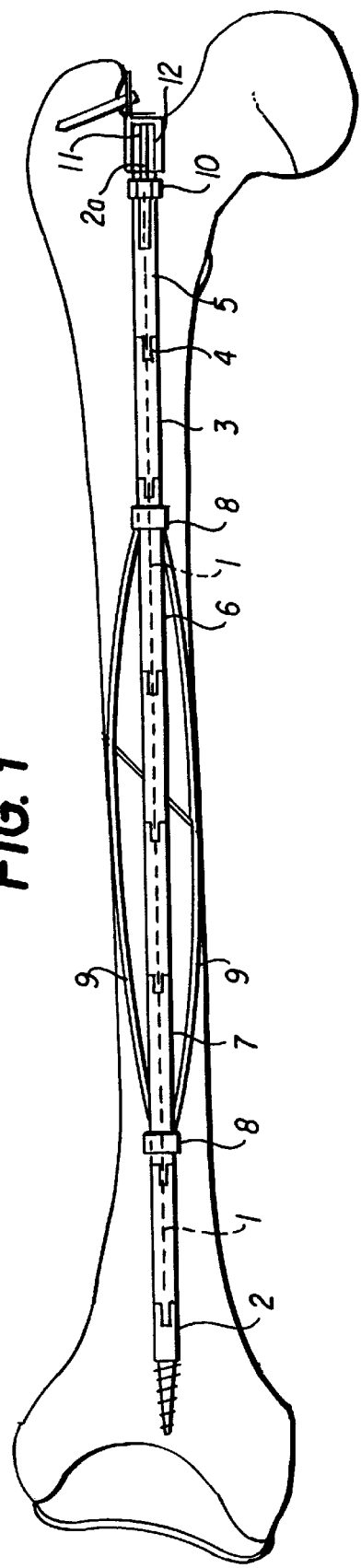
FIG. 1 is a representation of the device implanted into a femur bone.
Figure 4:
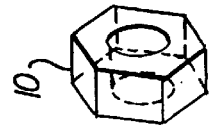
FIG. 4 is a representation of the nut 10.
Figure 3:
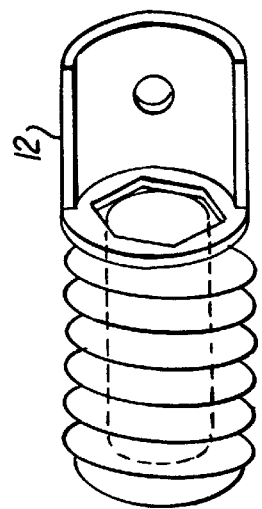
FIG. 3 is a representation of the anchor means 12.
Figure 2:
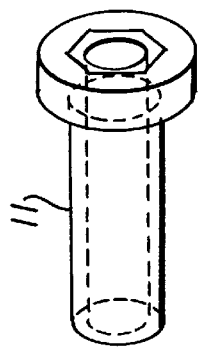
FIG. 2 is a representation of the bolt 11.
Figure 9:
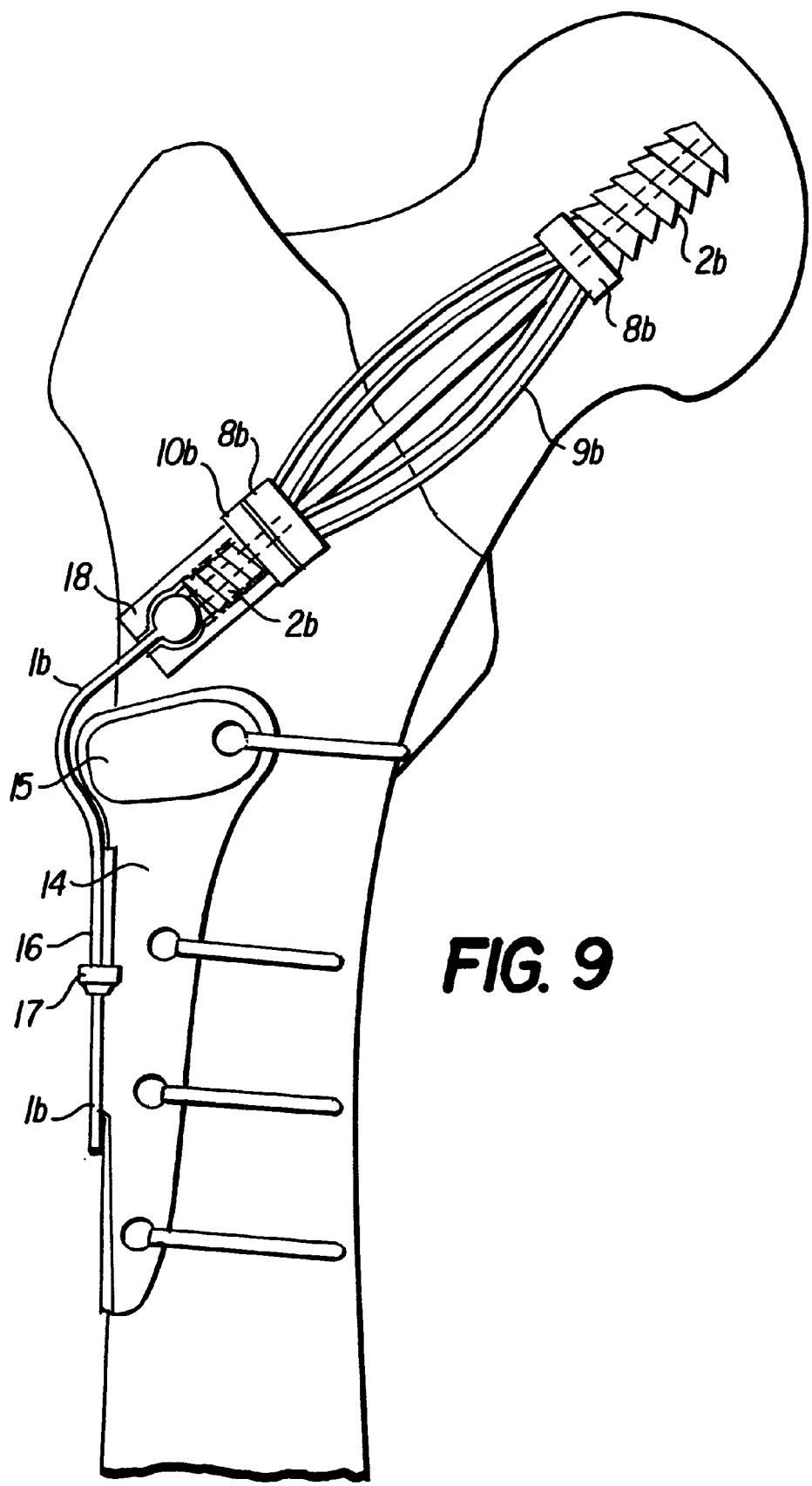
FIG. 9 is a representation of the device implanted into a proximal femur bone.

Referring now to the drawings the following detailed description of two embodiments, one for a long bone fracture and one for a proximal femur fracture will help understand how we apply the above mentioned principle of bi-axial prestressing.

The tendon 1 for the application of axial prestressing can be a wire-cable. Its one end is incorporated into an anchor means 2, which may be a self-taping screw, suitable for spongy bone. The head of the anchor means is cylindrical with two slots 4, dividing the perimeter of the cylinder into two protrusions which fit into the two slots of the preceding cylindrical body 3. The other end of the tendon is incorporated into a screw means 2a, for example a threaded bar.

The tendon is passing through cylinders. We have three kinds of cylinders depending on their position on the device and their use. All the cylinders except the last one 5 towards the end of the device near the body have two opposite facing slots 4 at both their ends, dividing the perimeter of the cylinder into two protrusions which fit into the two slots of the nearby cylinder, so as to allow the cylinders first to fit into one another and form a flexible bar, and second to transmit the torsion force which we apply on the torque means 5 to the anchor means 2.

The two cylinders 6, 7, which correspond to the focus of the fracture, have an overdrawn perimeter for part of their length, to provide place for attachment means 8, in which the deformable laminated springs 9 are adapted. The length of the slots of these two cylinders on the end where they fit into one another is longer, so as to allow them to come closer, compress the laminated springs and let them bow and exercise intramedullary pressure.

The torque means 5, placed last towards the end of the device near the body is of similar shape to the cylinders 3 along half of its length. The other half of its length, towards the end of the device, has the shape of a screw nut as regards its external shape. A nut screwdriver is adapted to this half of the torque means 5 to screw the anchor means 2, by screwing the whole device around itself. The internal cylindrical opening of the part of the torque means 5 which fits Into the cylinder 3 is of the same diameter as the openings of all the other cylinders so as to allow the tendon to pass through, whereas the part of the internal opening towards the end of the device is larger to let the threaded bar 2a adapted to the tendon fit into it and be stopped there so as to hold all the cylinders together.

A nut 10 is screwed around the threaded bar 2a to bring all the cylindrical bodies 3,6,7 and torque means 5 together and compress laminated springs 9, which by deforming laterally, exercise intramedullar pressure, i.e. transversal prestressing.

The bolt 11 is then screwed around the bar 2a after the nut 10, to apply tension to the tendon 1 with support on the anchor means 12 and on the bone, thus exercising axial prestressing, that is preloading of the bone.

Bolt 11 may be replaced by an element with grooves on its outer side. In the case of such an element when screwed inside the anchor means 12 and by compressing the bar 2a, it applies compression forces to the device, thus distracting the bone fragments when necessary.

The tendon 1b for the application of lateral prestressing can be a wire cable. Its one end may have the form of a ball which is attached to a bolt 18, which bolt is screwed around torque means 5b. Torque means 5b is actually the one end of an anchor means 2b, and serves to screw the anchor means into the bone. The other end of the anchor means 2b may be a self-taping screw, suitable for spongy bone. The body of the anchor means 2b is hollow because the anchor means is positioned with the help of a drill guide. Around the cylindrical part of anchor means 2b deformable elements 9b are disposed almost along the same direction, which are fixed at both their ends into attachment means 8b. Before screwing bolt 18 around the one end of anchor means 2b, we screw a nut 10b, which compresses the attachment means 8b between eachother, thus deforming the deformable elements 9b laterally. The deformable elements 9b fill up the Ward's Triangle and exercise pressure on the inner side of the bone (transversal prestressing).

A plate 14 is fixed with screws on the lateral cortex of the femur. This plate differs from the usual ones in two points. First it has a protrusion 15 on its head, which serves as a fulcrum for the tendon 1b to have a smooth change of direction of the tendon. Second, there is a cylinder 16 fixed on the plate's body. The tendon 1b is passing through this cylinder.

We exercise tension (lateral prestressing) on the tendon along its axis, with support against the cylinder 16. This tension may be easily measured and adjusted according to the necessities of the direction of the fracture, the weight of the patient and the form, dimensions and quality of the bone. This tension can be applied by means of a dynanmmetric tensioner, which in this case plays the role of a tension means. We then anchor the tendon on the plate with a securing means 17. This securing means 17 may be in the form of a deformable metal dip or cylinder, which can be deformed and pressed on the tendon In a fixed relationship.

What is claimed is:

1. A device for flexible fixation of long bone or proximal femoral fractures, said device comprising an elongate mechanical tendon adapted to apply axial prestressing or lateral prestressing to a fractured bone during fixation under tension in intramedullary position therein, said tendon having first and second ends with anchor means at the first end of said tendon and screw means at the second end of said tendon, a plurality of deformable elements held captive between said first and second ends and generally disposed about and along and substantially co-axial with the same longitudinal axis as said tendon and adapted to be positioned at the focus of the fracture when said tendon is in said intramedullary position for fixation, compression components for adjustably applying a compressive force to said deformable elements to cause lateral deformation thereof relative to said longitudinal axis adapted to transversely prestress the fractured bone at said focus, tension-applying elements comprising said anchor means and said screw means adapted to apply tension force to said tendon when in said intramedullary position for axial or lateral prestressing and fixation of the fractured bone simultaneous with said transverse prestressing, a plurality of cylindrical elements disposed about said tendon with attachment means spaced apart on two of said cylindrical elements for attaching the ends of said plurality of deformable elements thereto, said compression components being adapted to be screwed on said screw means whereby to bring said two cylindrical elements together to compress said deformable elements and deform them laterally, and thereby exercise intramedullary pressure transverse prestressing of the fractured bone.

2. The device of claim 1, wherein said compression components include means for applying torque to said anchor means for screwing said tendon onto the anchor means.

3. The device of claim 1, wherein said attachment means are slidable for retaining both ends of said deformable elements relative to said tendon, said attachment means coating with said compression components for said compression of said deformable elements and said lateral deformation thereof to a desired extent to enable distraction of bone fragments.

4. The device of claim 1, comprising bolt means and second anchor means at said second end of said tendon, said bolt means and second anchor means cooperating with said screw means at said second end to apply a tension force to said tendon.

5. The device of claim 4, comprising third anchor means and securing means at said second end of said tendon and co-acting to maintain said tension force applied to said tendon.

6. The device of claim 1, wherein said cylindrical elements have end slots to enable mating of adjacent ones of said cylindrical elements on said tendon and thereby form a flexible bar.

7. The device of claim 6, wherein said end slots of at least two adjacent ones of said cylindrical elements are shaped to enable said at least two cylindrical elements to be brought closer together for compression of said deformable elements.

8. The device of claim 6, wherein the first-mentioned anchor means has a slotted cylindrical head adapted to mate with the end slots of the adjacent one of said cylindrical elements.

9. The device of claim 1, wherein said tension-applying elements further include a bolt adapted to be screwed onto an end of said anchoring element, and wherein said first end of said tendon has the shape of a ball adapted to mate with a socket within said bolt.

10. The device of claim 5, wherein said third anchor means comprises a plate and a cylinder, said cylinder being attached to said plate.

11. The device of claim 10, wherein said plate includes a protrusion constituting a fulcrum for said tendon.

12. The device of claim 1, including a biocompatible plate covering the entirety of the surface of said device outside the fractured bone to provide a smooth external surface thereof.

* * * * *